(12) United States Patent
Guo et al.

(10) Patent No.: US 9,799,100 B2
(45) Date of Patent: Oct. 24, 2017

(54) INTEGRATION OF T2-PREPARATION AND MOTION TRACKING IN MAGNETIC RESONANCE IMAGING

(71) Applicant: THE JOHNS HOPKINS UNIVERSITY, Baltimore, MD (US)

(72) Inventors: Liheng Guo, Baltimore, MD (US); Daniel A. Herzka, Rockville, MD (US)

(73) Assignee: The Johns Hopkins University, Baltimore, MD (US)

(*) Notice: Subject to any disclaimer, the term of this patent is extended or adjusted under 35 U.S.C. 154(b) by 186 days.

(21) Appl. No.: 14/784,963

(22) PCT Filed: Apr. 15, 2014

(86) PCT No.: PCT/US2014/034115
§ 371 (c)(1),
(2) Date: Oct. 16, 2015

(87) PCT Pub. No.: WO2014/172328
PCT Pub. Date: Oct. 23, 2014

(65) Prior Publication Data
US 2016/0078604 A1    Mar. 17, 2016

Related U.S. Application Data

(60) Provisional application No. 61/812,321, filed on Apr. 16, 2013.

(51) Int. Cl.
*G06K 9/00* (2006.01)
*G06T 5/00* (2006.01)
(Continued)

(52) U.S. Cl.
CPC ............ *G06T 5/002* (2013.01); *A61B 5/0055* (2013.01); *A61B 5/055* (2013.01); *A61B 5/721* (2013.01); *A61B 5/7207* (2013.01); *G01R 33/5602* (2013.01); *G01R 33/5676* (2013.01); *G01R 33/56509* (2013.01); *G06T 7/0012* (2013.01);
(Continued)

(58) Field of Classification Search
None
See application file for complete search history.

(56) References Cited

U.S. PATENT DOCUMENTS 8,183,864 B2    5/2012    Xu
2005/0065430 A1    3/2005    Weithoff et al.
(Continued)

FOREIGN PATENT DOCUMENTS

JP    2009-160378 A    7/2009

*Primary Examiner* — Atiba O Fitzpatrick
(74) *Attorney, Agent, or Firm* — Johns Hopkins Technology Ventures (57) ABSTRACT

An embodiment in accordance with the present invention provides concurrent measurement of motion during T2-weighted magnetic resonance imaging. The present invention combines T2 preparation, a module used to impart T2 contrast, and motion measurement, tracking, and/or correction. The present invention provides for the expedition of more efficient motion compensation during T2-weighted imaging. The proposed invention can be used to provide a variety of measurements of motion, with no overhead in imaging time. The proposed invention also enables T2 contrast imaging to be executed while a subject is breathing freely, without the additional time cost associated with the standard motion tracking methodologies.

15 Claims, 7 Drawing Sheets

(51) Int. Cl.
       A61B 5/055      (2006.01)
       A61B 5/00       (2006.01)
       G01R 33/56      (2006.01)
       G01R 33/567     (2006.01)
       G01R 33/565     (2006.01)
       G06T 7/00       (2017.01)
       G06T 7/207      (2017.01)

(52) U.S. Cl.
       CPC .... *G06T 7/207* (2017.01); *G06T 2207/10088* (2013.01); *G06T 2207/30048* (2013.01); *G06T 2207/30092* (2013.01)

(56) References Cited

U.S. PATENT DOCUMENTS

| | | |
|---|---|---|
| 2006/0224062 A1 | 10/2006 | Aggarwal et al. |
| 2012/0194186 A1 | 8/2012 | Rehwald et al. |

INTEGRATION OF T2-PREPARATION AND MOTION TRACKING IN MAGNETIC RESONANCE IMAGING

CROSS-REFERENCE TO RELATED APPLICATIONS

This application is a 35 U.S.C. §371 U.S. national entry of International Application PCT/US2014/034115 having an international filing date of Apr. 15, 2014, which claims the benefit of U.S. Provisional Application No. 61/812,321, filed Apr. 16, 2013, the content of each of the aforementioned applications is herein incorporated by reference in their entirety.

FIELD OF THE INVENTION

The present invention relates generally to medical imaging. More particularly, the present invention relates to a method of measuring motion during magnetic resonance imaging.

BACKGROUND OF THE INVENTION

Magnetic resonance imaging (MRI) is an indispensible modality in medical imaging primarily for its ability to distinguish among a wide array of human tissues as well as among their pathologies. There is an immense body of MRI methodologies at one's disposal to generate diagnostically meaningful contrast to target the medical conditions in question. In general, transverse magnetizations are generated by radiofrequency (RF) "excitation" in the imaged subject, and data acquisition measures the transverse magnetizations in the spatial frequency transform space (the "k-space"). The resultant image is a map of the transverse magnetizations in the imaged slice or volume.

The most common physical properties by which MRI distinguish tissue types and diseases are proton density, T1 (spin-lattice relaxation time), and T2 (spin-spin relaxation time). T2-weighted imaging, in particular, where image contrast is primarily based on differences in tissue T2 values, is essential in the evaluation of the cardiac and cardiovascular systems, the central nervous system, and the musculoskeletal system. It allows for visualization, for instance, of tissue edema, coronary artery patency, the distribution of cerebrospinal fluid and the synovial fluid.

T2-weighted imaging was originally achieved using the spin echo imaging, and later the turbo spin echo imaging, both of which are currently in clinical use. In the spin echo and its variants, transverse magnetizations are generated by excitation and are allowed to decay exponentially under the influence of T2. Imaging data acquisition executes at a desired time delay after excitation, known as the echo time (TE). In spin echo, the acquisition only samples a small portion of the k-space and is therefore short enough to be considered instantaneous compared to the T2 decay itself. In turbo spin echo, the acquisition is longer and it takes place during a significant portion of the T2 decay process. In such case, one acquires the most important portion of k-space (the center and near-center components) at TE.

T2 preparation, or "T2 Prep", has been an alternative to spin echo-based imaging. Similar to spin echo, T2 Prep uses the radiofrequency manipulation of transverse magnetizations to enhance T2 contrast. Transverse magnetizations are generated and allowed to decay under T2, and refocusing pulses are used to prevent incoherence buildup among spins that resonate at different frequencies. However, in T2 Prep, special care is taken in the RF pulse design to reduce effects of imperfections in B0 (MR scanner longitudinal main field) and B1 (MR scanner transmitter RF field). Also, the transverse magnetizations are restored to the longitudinal configuration when the desired TE is reached, ready for use with any desired imaging acquisition that follows. (Usually a "spoiler" is required after longitudinal restoration to eliminate any residual left in the transverse configuration.)

Figure 1:
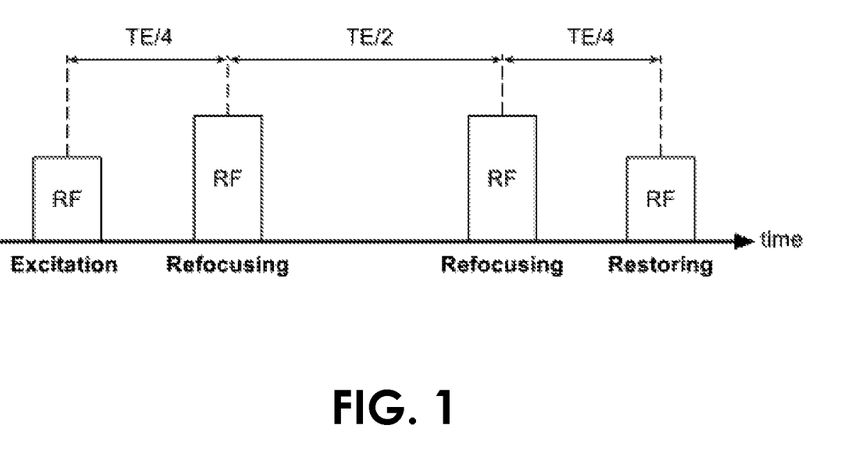

FIG. 1 displays a typical and idealized T2 Prep module. An excitation RF pulse (typically a 90° pulse) is used to transfer magnetizations from the longitudinal configuration into the transverse configuration. The magnetizations start to experience T2 decay immediately. During the decay, a train of refocusing RF pulses (typically 180° pulses) repeatedly refocus the spins to undo the effects of off-resonance. During this time, transverse magnetizations of different T2's decay at different rates, establishing T2 contrast among them. Finally, a restoring RF pulse (typically a −90° or equivalent pulse) is used to return the magnetizations to its longitudinal configuration, carrying in their magnitude the desired T2-weighted contrast.

Figure 2:
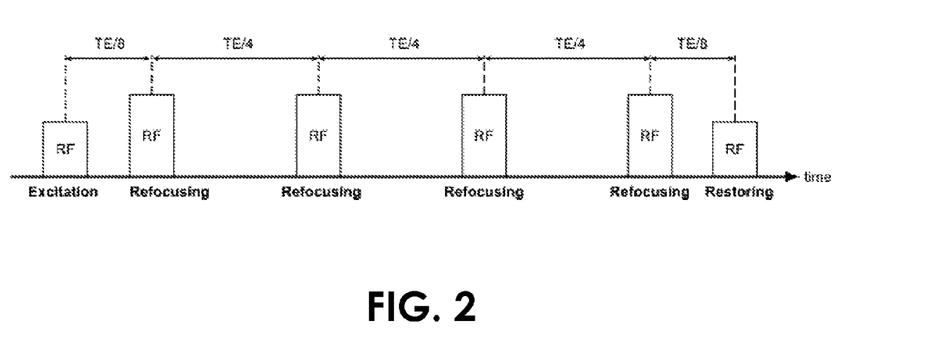
FIG. 2 illustrates a typical T2 Prep with four refocusing pulses (180 degree pulses), which are placed between the excitation pulse (90 degree pulse or equivalent) and the restoring pulse (−90 degree or equivalent). As with the two-refocusing T2 Prep, the RF pulses here may be hard RF pulses (shown here), shaped slice selective pulses, composite pulses, or adiabatic pulses.

The configuration of a T2 Prep may vary in a few ways. The refocusing pulses of T2 Prep may be simple hard pulses, composite pulses (e.g. MLEV-weighted composite pulses (1-3)), or adiabatic pulses (4). The number of refocusing pulses is typically 2 or 4 in practice. The number is also typically even, to exploit B1 insensitivity. The 4-refocusing configuration is shown in FIG. 2.

In typical imaging applications, the duration of T2 Prep is set to be in the vicinity of the tissue T2s themselves—usually between 20 to 100 ms. After a T2 Prep module, the differences in transverse magnetizations among tissue types are maximized to reflect their range of T2 values. However such T2 contrast lasts only briefly before the signal is degraded by other sources (e.g. T1 relaxation). Thus, to reflect the most accurate T2-weighting, imaging data acquisition must start as early as possible after the end of the T2 Prep module. It is therefore very important to minimize the time delay between the end of the T2 Prep module and the onset of imaging data acquisition. In practice, however, a delay is often inevitable due to other preparations necessary before imaging (e.g. fat saturation, conventional motion tracking using pencil-beam navigator, discussed below). The imaging data acquisition must also finish before the T2 contrast degrades, in other words, within 1× or 2× tissue T2 after the T2 Prep module.

Figure 3:
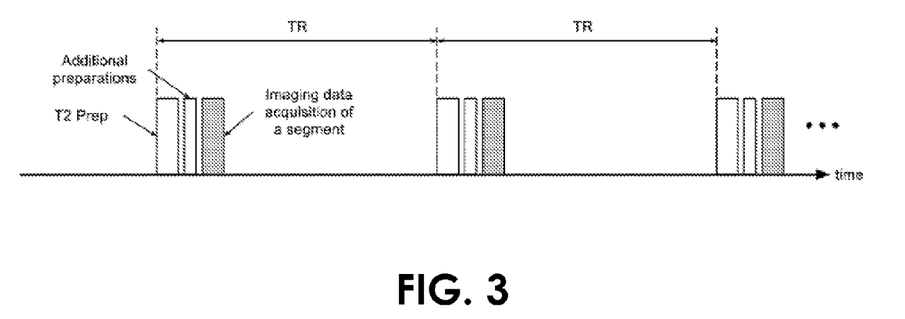
FIG. 3 illustrates repeated executions of T2 Prep and imaging data acquisition: the window for imaging data acquisition is short because the degradation of T2 contrast after each T2 Prep module due to imaging. As a result, to acquire all necessary data to reconstruct an image, T2 Prep and imaging need to be executed repeatedly, with a segment of k-space acquired in each repetition. Note that additional preparation such as fat saturation or the pencil-beam navigator may be necessary before imaging window starts. This presents a significant loss of imaging time and requires more repetitions to be performed. The interval between every two consecutive repetitions is known as repetition time (TR).

As a result, the acquisition window following each T2 Prep module is brief, with a duration similar to tissue T2 itself (20 to 100 ms). Usually one can only acquire a small portion of all necessary imaging data (a "segment" of k-space) due to a large variety of physiological and hardware limitations in acquisition speed. Hence, the T2 Prep-imaging tandem is executed repeatedly until all segments of the k-space are acquired, as shown in FIG. 3.

Figure 4:
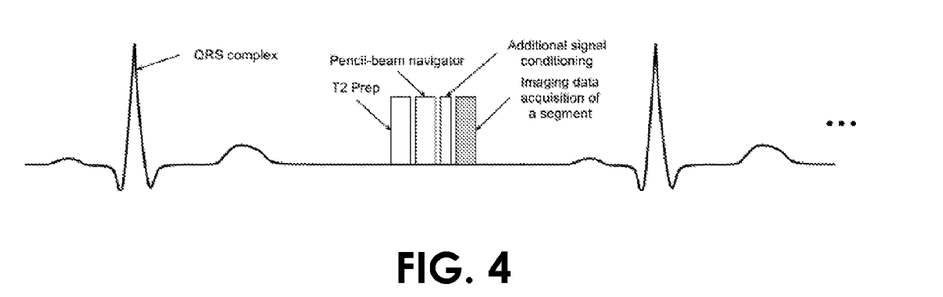
FIG. 4 illustrates typical usage of T2 Prep in free-breathing cardiac imaging: a T2 Prep and the ensuing segment imaging are executed every one or two heartbeats, at a desired delay time after each cardiac synchronization trigger (usually the QRS complex of each heartbeat). Note additional preparations such as motion tracking and fat saturation are necessary before imaging data can be acquired. The duration of the conventional pencil-beam navigator, for example, is usually equal or greater than the imaging data acquisition itself. In this figure, the durations of the modules are approximately drawn to scale with respect to one another and to the RR interval of the ECG.

For T2-weighted cardiac imaging, in particular, a T2 Prep and the ensuing segment imaging are executed every one or two heartbeats, at a desired delay time after each cardiac synchronization trigger (usually the QRS complex of each heartbeat). FIG. 4 shows one repetition of such an arrangement. To track respiratory motion, the conventional pencil-beam navigator is executed, usually between T2 Prep and imaging. This causes a significant imaging delay during which the fresh T2 contrast degrades for a duration comparable to that of the imaging window itself. If any kind of motion data can be collected during the T2 Prep module, the delay time before imaging onset can be significantly reduced and the imaging window can be extended. This would present a significant saving to the number of segment repetitions required. If the order of T2 Prep and the respiratory pencil beam navigator were reversed, the time between T2 Prep and imaging could be reduced. However, this would degrade the quality of motion information obtained with the respiratory navigator, as the interval between the measurement of motion and actual imaging would increase significantly with possible detrimental effects for imaging.

In the standard design of T2 Prep, however, no imaging data or motion data is collected during T2 Prep. This amounts to a dead time comparable to the duration of the imaging window itself. The reason is, during T2 Prep, the transverse magnetizations of imaged tissue are interacting with RF pulses that disperse and refocus them. Measuring such magnetizations for imaging would not yield data consistent with the rest of the imaging data, leading to artifacts and unacceptable image quality.

MRI is a relatively slow imaging modality and motion of the sample or the subject causes significant image artifacts. In virtually all MRI scenarios, considerable efforts must be made to avoid motion in order to prevent severe corruption of image quality in the form of blurring, smearing, and ghosting. When motion is inevitable, it must be accurately tracked so that imaging data can be collected in synchrony with the motion cycle, or that the imaging data can be corrected for motion artifacts. Both cardiovascular and respiratory motion are relevant, though other types of motion exist and must also be addressed: voluntary and involuntary motion by the patient or subject, peristaltic motion in the gut, swallowing, head motion due to cardiac pulsatility, etc.

In the abdomen, where respiratory motion is problematic, T2-weighted imaging has been restricted to breath-hold imaging. Because respiratory motion in the abdomen is pervasive and nonrigid, complex measurements of the motion field is required if motion is to be corrected. This type of motion is very important when imaging organs in the abdominal cavity such as the liver, the kidneys, the pancreas, etc.

The heart is also imaged with T2-weighted MRI because myocardial edema can be assessed this way. It is a highly challenging region due to its constant motion, which is generally a mix of two parts: intrinsic cardiac motion and respiratory motion. To track these two types of motion, T2-weighted cardiac imaging borrows standard techniques from general cardiac imaging: for cardiac motion, additional electronics such as the electrocardiogram (ECG) can be used. To track respiratory motion, an external mechanical device known as the respiratory bellow can be used. As an alternative, the MR scanner may periodically acquire additional motion-tracking data known as the "navigator" to track respiratory position.

When T2 Prep is used in regions affected by respiratory motion, such as in cardiac T2-weighted imaging mentioned earlier, a "pencil beam navigator" is used as the standard method for tracking respiratory motion. The pencil beam navigator, also known as "NAV" or simply "the navigator," is a dedicated process during which a 2D-selective excitation generates MR signal from a narrow column of tissues to indicate its 1D displacement. The column is usually placed across the lung-liver interface. Typically, each pencil-beam navigator lasts from 20 to 50 ms, and is executed between T2 Prep and imaging data acquisition. The delay before imaging window is significant, because its duration is comparable to the imaging window itself (1× or 2× tissue T2). This is a significant price to pay for the readout of a single point of respiratory position. Additionally, the use of the pencil-beam navigator also assumes respiratory motion to be 1D (namely in the foot-head direction), permitting only gating and 1D translational correction of respiratory motion. Though multiple navigators can be applied and used for more complex (e.g. affine) motion correction, the delay time due to multiple navigators can be prohibitive for maintaining T2 contrast.

Although during T2 Prep the transverse magnetizations are in flux and unsuitable for imaging, it is noteworthy that the magnetization is still suitable for motion tracking. This suggests that motion measurements can be performed during T2 Prep. Because motion tracking in MRI operates on much less information than image formation, it usually requires lower signal quality and less data. Researchers have reported numerous successful tracking techniques using limited data, including low resolution images, projections of the imaged slice, the average signal of the imaged slice, or some other small subsets of imaging data itself. If any of these limited-data motion measurements is merged into T2 Prep, motion can be tracked in 2 or more dimensions.

It is therefore desirable to provide a method of MRI imaging that allows for accurate acquisition of MRI in areas of the body with at least one source of motion without image artifacts.

SUMMARY OF THE INVENTION

The foregoing needs are met, to a great extent, by the present invention, wherein in one aspect a method of obtaining a corrected image of a subject includes using a T2 preparation module comprising RF pulses to obtain a base magnetic resonance (MR) image of the subject. The method also includes inserting motion tracking elements into the T2 preparation module. Additionally, the method includes determining motion information from the motion tracking elements and correcting the base MR image of the subject using the motion information.

In accordance with an aspect of the present invention, the method further includes the motion tracking elements being interspersed between 2 consecutive RF pulses. The method can be used for any of the following: 1D projection of 2D and 3D volumes, tracking and correction of respiratory displacement, tracking the respiratory displacement of the heart, the movement of the heart itself caused by the cardiac cycle, and affine or non-rigid movement of the abdomen. The RF pulses can take the form of at least one of hard pulses, shaped or slice selective pulses, MLEV composite pulses, adiabatic pulses, and any other equivalent pulses for excitation, refocusing, and restoring. The method can also include using signal conditioning and imaging data acquisition after using the T2 preparation module. The motion tracking can take the form of at least a projection, a radial readout, and/or any other motion-measurement readout. In addition, multiple projections can be taken along more than one axis, and data can be phase encoded in 2D and 3D if very low resolution images are desired.

In accordance with another aspect of the present invention, the method further includes using a magnetic resonance imaging machine to execute steps of the method. Steps of the method are executed with a non-transitory computer readable medium. A computing device is networked to the magnetic resonance imaging machine. The computing device is loaded with a non-transitory computer readable medium programmed for executing steps of the method.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and:

FIG. 1 illustrates a typical idealized T2 preparation (T2 Prep) module: having an excitation pulse (a 90 degree pulse or equivalent) to generate transverse magnetizations, followed by one or more pairs of refocusing pulses (180 degree pulses or equivalent), and finishing with a restoring pulse (a −90 degree or equivalent pulse) which restores the transverse magnetization into the longitudinal direction. The duration between the excitation and restoring pulses is known as the TE (echo time) for the T2 Prep and a spin echo is formed at the midpoint of the excitation and restoring pulses. This figure shows one pair of focusing RF pulses, placed at ¼ and ¾ TE respectively. A spoiler gradient (not shown) is usually applied after the restoring pulse to eliminate any residual transverse magnetization due to the non-ideal nature of RF pulses. The RF pulses themselves can take many forms, such as simple block or hard RF pulses (shown here), shaped pulses to be combined for slice selective T2 Prep, composite pulses that improve performance, and adiabatic pulses for best performance under B1 transmit field inhomogeneities.

FIG. 6A illustrates a schematic of one example of a multi-projection implementation of T2 Prep with motion detection capabilities. A multiplicity of readouts can be inserted due to the generally long T2 Prep module duration and the generally short time required to acquire a projection. This example shows the RF and gradient waveforms of a T2 Prep module with three orthogonal projections with balanced gradients inserted into the center of the innermost pair of refocusing RF pulses. The readouts need not be in the order illustrated here in this example (x, y, then z), nor do they need to be all consecutively inserted between the innermost time gap between the RF pulses. Hence, a large number of short projection readouts could be inserted between any consecutive pair of RF pulses, and acquire projections along any arbitrary direction. For illustration purposes, the temporal footprint for both RF pulses and the readout gradients have been exaggerated in this figure; in actuality the temporal gaps between RF pulses allow for more projection readouts to be inserted.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

In this invention, readouts are inserted into the T2 Prep module for motion tracking. Any type and any number of readouts can be inserted between any two contiguous RF pulses of the T2 Prep module, depending on the available time gap between the RF pulses. The readouts should not overlap with the RF pulses to prevent artifacts in the image acquired afterward. In general, shorter groups of readouts such as individual projections provide basic motion information, and will be described herein. On the other hand, the more time-consuming readout may provide enough information for motion-field mapping.

As with the conventional T2 Prep, any type of RF pulses (e.g. hard pulse, shaped slice selective pulses, MLEV composite pulses, adiabatic pulses) may be used according to the imaging application. Also, immediately following each T2 Prep module, other signal conditioning (e.g. spoiler, fat saturation) and imaging data acquisition can take place as needed. Motion tracking achieved by this invention can allow, for example, the removal of the conventional pencil-beam navigator, and the acquisition of motion field of nonrigid motion.

Projections have been one of the most frequently used motion tracking techniques in MRI. A projection is the imaged volume or slice as projected onto a straight-line path in space, and can be used to derive motion in a number of applications. As explained by the projection slice theorem, one can easily obtain a projection of the imaged volume or slice by acquiring a straight-line path in k-space at the same orientation as in space. This acquisition is typically fast, ranging from below 1 ms to approximately 3 ms. Thus even for a T2 Prep module of limited duration (e.g. 20 ms), the acquisition of one or more projections can be easily inserted, to produce 1D images at one or more orientations. These projections can then be post-processed to derive motion in one or more orientations.

Figure 5A:
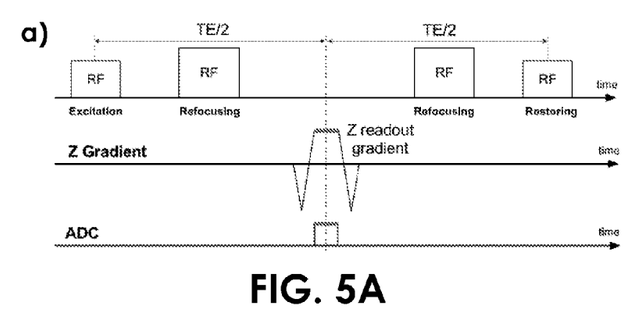
FIG. 5A illustrates RF and gradient waveforms for a single-projection, two-refocusing implementation of the proposed invention. In this example, the projection readout is acquired with a balanced gradient and is aligned with the center of T2 Prep module. The ADC (analog-to-digital conversion), also aligned, measures the echo formed there. The projection is along the MR scanner's z-axis, and only two refocusing RF pulses are used. However, the projection readout can be sampled at any time in the T2 Prep module between the first and last RF pulses. It can be oriented along any axis in 3D, and more than one pair of refocusing pulses can be used.
Figure 5B:
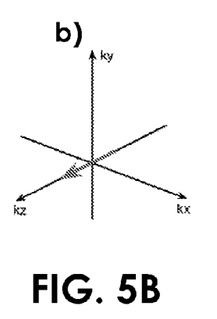
FIG. 5B illustrates the corresponding k-space trajectory of the projection readout shown in a).

FIGS. 5A and 5B show an example of a single-projection implementation of the proposed invention. In this particular example, a single projection along the z-axis of the imaged volume is inserted between the pair of refocusing pulses of the T2 Prep module, although projection can align with any axis and more than one pair of refocusing pulses can be used. The inserted readout gradient should be fully balanced such that no residual gradient moment (gradient waveform area) is left. However, taking into account the refocusing action of RF pulses, it may be possible to use individually unbalanced gradients that as a whole are balanced. The z-projection echo time aligns with the midpoint of the T2 Prep module, although the alignment is not necessary for the proposed invention.

Figure 6A:
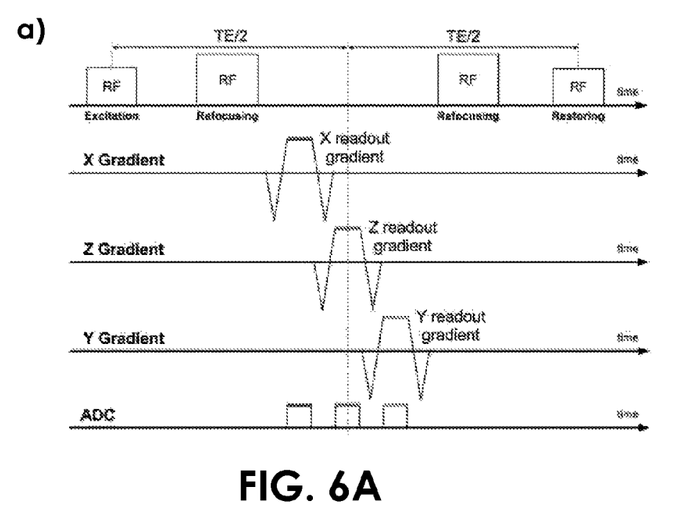
FIG. 6B illustrates The corresponding k-space trajectories of the projection readouts shown in a).
Figure 6B:
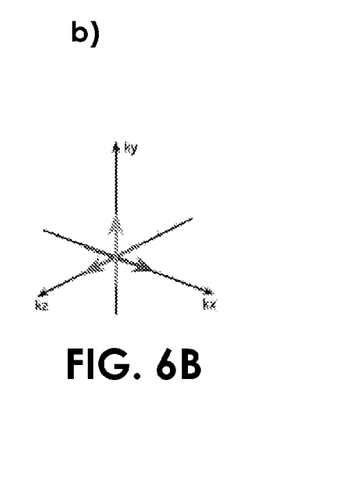

Multiple projection readouts along more than one axis (e.g. x, y, z) can be inserted into the T2 Prep module, into one or more time gaps between the RF pulses. FIGS. 6A and 6B show the RF and gradient waveforms of a T2 Prep module with three orthogonal projections inserted into the middle of the innermost pair of refocusing RF pulses. Again, the inserted readout gradients are fully balanced for each axis. The readouts need not be in the order illustrated here in this example (x, y, then z), nor do they need to all consecutively inserted between the innermost time gap between the RF pulses.

Figures 7A, 7B:
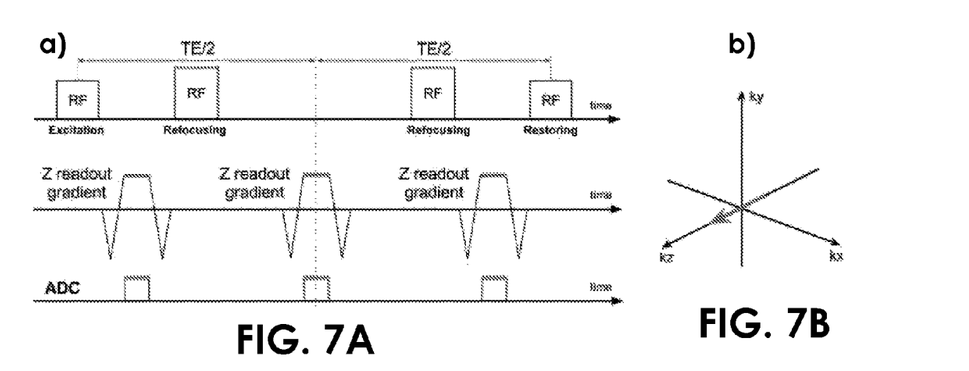
FIG. 7A illustrates a Schematic of one example of a multi-projection implementation of T2 Prep with motion detection, where three motion-measuring projection readouts are inserted, all along the same axis, but in different temporal positions throughout the T2 Prep module between consecutive RF pulses. Because position along is measured at three points in time (in this case along the z-axis), velocity and acceleration can be calculated along the projection direction. For illustration purposes, the temporal footprint for both RF pulses and the readout gradients have been exaggerated in this figure; in actuality the temporal gaps between RF pulses allow for more projection readouts to be inserted.
FIG. 7B illustrates the corresponding k-space trajectory of each projection readout shown in a).

Readouts can be inserted between any pair of consecutive RF pulses. Furthermore, it is not difficult to see that if more than one readout is inserted, all or some in the same direction, it should be possible to acquire a measure not only of displacement (e.g. shift relative to a baseline measurement) but also of velocity of motion. For example, if three motion-measuring readouts were placed in the T2 Prep sequence, as illustrated in FIGS. 7A and 7B, the difference in displacement, divided by the small time shift between the readouts, would allow two separate measurements of velocity. Hence it would be possible to correct, modify or accept/reject data based not only on the position of the tissue of interest, but also on whether the motion is accelerating, decelerating or stationary. With three readouts, it would also be possible to get a measure of acceleration. For the same purposes, multi-echo readouts (preferably fully balanced readouts) could also be used for measurements of velocity and acceleration.

Projections need not to be acquired along the axes in k-space; any readout passing through the center of k-space can be thought of as a projection along an arbitrary angle, which is known as a radial readout. There are existing imaging techniques that acquire radial readouts continuously for both motion measurement and imaging data, in both 2D and 3D. Each radial readout takes less than 1 ms to approximately 3 ms to acquire. Several such radial readouts can be inserted between any two RF pulses of the T2 Prep module, in the same way orthogonal projections are inserted. These inserted radial readouts are used together with those acquired after T2 Prep for motion mapping, although these two types of readouts may exhibit different contrasts.

For abdominal imaging where the motion is nonrigid and pervasive, motion field mapping of the imaged anatomy is required to fully capture the motion. It necessitates more complex motion tracking beyond the pencil-beam navigator and its 1D displacement measurement. It requires significantly more motion data collection, which may compete with imaging data collection for the viable time window after T2 Prep. Suitable for this problem there are some existing techniques where any MR data collected serve the dual purpose of image formation and motion measurement in 2D and 3D. These techniques are fully or partially "radial acquisitions" where data acquisition consists of k-space trajectories that cross center k-space origin. Also feasible is the use of spherical navigators, which coarsely sample a 3D sphere at the center of k-space to achieve motion compensation based on rigid body motion. Additionally, multi-echo readouts, e.g. the SPIDER, could also be applied to generate multi-dimensional data and better motion detection. Hence, readouts of two or more echoes could be used to increase the amount of data sampled for motion estimation.

If such data measurements are inserted into the T2 Prep module, motion field mapping is possible without imaging time overhead. Although the inserted data measurements take place before the proper T2 contrast is ready, they can still be used in conjunction with those acquired just after the module for motion tracking (since motion field mapping operates on the spatial structure of images rather than any specific image contrast). The duration of a T2 Prep module is sufficient to permit enough motion data to be acquired to construct the motion field without compromising the imaging window following the T2 Prep module.

Though not discussed herein, the motion measurements obtained with the proposed technique can be used for motion compensation such that imaging data is modified based on the measurements made during the combined T2-prep/motion measurement sequence.

Any other motion-measurement technique can be inserted into the T2 Prep module, as long as its k-space trajectory is fully balanced (i.e. it refocuses all transverse magnetization at the end of motion measurement) and its temporal footprint fits within the T2 Prep module. Examples of such trajectories include single "blades" of the PROPELLER method, the orbital navigator, the spiral navigator, and near-center Cartesian readouts.

T2-weighted cardiac imaging is a key technique for visualizing myocardial edema and coronary artery patency, especially after a significant event such as myocardial infarction or cardiac ablation procedure. During these lengthy free-breathing scans, the proposed invention can track respiratory motion at no additional time cost and avoid the need for the conventional pencil-beam navigator. As discussed earlier, since the pencil-beam navigator usually occupies as much time as the imaging window itself, removing it by using this invention can potentially double the duration of each imaging window and therefore cut the overall scan time by half.

A T2 Prep module used in cardiac studies typically has a short duration of approximately 50 ms. Therefore it is best suited for housing one or several orthogonal projections. Although not necessary for this invention, the RF pulses in a T2 Prep module are usually spatially nonselective. In such case, the signals generated during T2 Prep will reflect the entire imaged volume. In other words, bulk motion in the volume can be captured in all three dimensions by the orthogonal projections. In case of spatially selective RF pulses, projections are aligned along the in-plane dimensions of the imaged slice and will reflect motion therein.

The post-processing techniques for extracting motion from the projections can be similar to those used for the conventional pencil-beam navigator, but repeated on each orthogonal projection to include information measured from all orthogonal axes. Because all axes are monitored for motion, motion tracking is expected to be more precise than the pencil-beam navigator.

The proposed invention makes it possible for motion field mapping concurrent with T2-weighted abdominal imaging without burdening the post-T2 Prep imaging window. Radial readouts are inserted into T2 Prep modules, and these readouts, along with acquired after the T2 Prep modules, are combined for motion field reconstruction. The motion field, in turn, corrects the post-T2 Prep imaging data to form a motion-free image with proper T2 contrast. In abdominal imaging where motion is fairly slow but pervasive and nonrigid, motion correction by motion field is important for obtaining artifact-free images. The function and pathology of the liver, spleen, and pancreas, and kidney are of primary interest for motion-compensated T2-weighted abdominal imaging.

It should be noted that the methods described herein can be executed with a program(s) fixed on one or more non-transitory computer readable medium. The non-transitory computer readable medium can be loaded onto a computing device, server, imaging device processor, smartphone, tablet, phablet, or any other suitable device known to or conceivable by one of skill in the art. It should also be noted that herein the steps of the method described can be carried out using a computer, non-transitory computer readable medium, or alternately a computing device, microprocessor, or other computer type device independent of or incorporated with an imaging or signal collection device. The computing device can be integrated with the imaging device for collecting data or can be networked by wire or wirelessly with the imaging device. Indeed, any suitable method of calculation known to or conceivable by one of skill in the art could be used. It should also be noted that while specific equations are detailed herein, variations on these equations can also be derived, and this application includes any such equation known to or conceivable by one of skill in the art. A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method of obtaining a corrected image of a subject comprising:
   using a T2 preparation module comprising RF pulses and gradients to obtain a base magnetic resonance (MR) image of the subject;
   inserting motion tracking elements into the T2 preparation module;
   determining motion information from the motion tracking elements; and
   correcting the base MR image of the subject using the motion information.

2. The method of claim 1 further comprising interspersing said motion tracking elements between 2 consecutive RF pulses.

3. The method of claim 1 further comprising using the method for 1D projection of 2D and 3D volumes.

4. The method of claim 1 further comprising for tracking and correction of respiratory displacement.

5. The method of claim 4 further comprising tracking one of the respiratory displacement of the heart and the motion of the heart itself due to cardiac contraction.

6. The method of claim 1 further comprising tracking affine or non-rigid movement of the abdomen.

7. The method of claim 1 further comprising using RF pulses taking the form of at least one of hard pulses, shaped slice-selective pulses, MLEV composite pulses, adiabatic pulses, or any other equivalent pulses for excitation, refocusing, and restoring.

8. The method of claim 1 further comprising using signal conditioning and imaging data acquisition after using the T2 preparation module.

9. The method of claim 1 further comprising using the motion tracking element that comprises a projection.

10. The method of claim 9 further comprising inserting multiple projections along more than one axis.

11. The method of claim 1 further comprising using the motion tracking element comprising radial readouts.

12. The method of claim 1 further comprising using the motion tracking element taking the form of a motion-measurement readout.

13. The method of claim 1 further comprising using a magnetic resonance imaging machine to execute steps of the method.

14. The method of claim 1 further comprising executing steps of the method with a non-transitory computer readable medium.

15. The method of claim 13 further comprising using a computing device networked to the magnetic resonance imaging machine, the computing device being loaded with a non-transitory computer readable medium programmed with steps for executing the method.

* * * * *